United States Patent
Kalinski et al.

(12) 
(10) Patent No.: US 6,648,899 B2
(45) Date of Patent: Nov. 18, 2003

(54) MULTI-POSITION MENISCAL NEEDLE HOLDER

(75) Inventors: Robert J. Kalinski, Milford, NJ (US); Michael S. Pohle, Flemington, NJ (US); Jay Arthur Esch, River Falls, WI (US)

(73) Assignee: Ethicon, Inc., Somerville, NJ (US)

( * ) Notice: Subject to any disclaimer, the term of this patent is extended or adjusted under 35 U.S.C. 154(b) by 78 days.

(21) Appl. No.: 09/752,604

(22) Filed: Dec. 29, 2000

(65) Prior Publication Data

US 2002/0087172 A1 Jul. 4, 2002

(51) Int. Cl.[7] ............................................. A61B 17/04
(52) U.S. Cl. ........................ 606/148; 206/365; 604/198
(58) Field of Search ............................. 606/144, 147, 606/148, 232, 222, 80, 96–98; 112/167, 221; 206/363, 364, 365, 366, 438, 485; 408/72 R; 604/263, 192, 198

(56) References Cited

U.S. PATENT DOCUMENTS

| 599,561 | A | * | 2/1898 | Hopewell ................... 112/221 |
| 3,134,380 | A | * | 5/1964 | Armao ........................ 604/198 |
| 4,006,747 | A |  | 2/1977 | Kronenthal et al. |
| 4,349,022 | A |  | 9/1982 | Ishikawa |
| 4,795,432 | A | * | 1/1989 | Karczmer ................... 604/263 |
| 4,974,728 | A |  | 12/1990 | Colton |
| 5,031,775 | A |  | 7/1991 | Kane |
| 5,085,639 | A |  | 2/1992 | Ryan |
| 5,088,982 | A |  | 2/1992 | Ryan |
| 5,320,633 | A |  | 6/1994 | Allen et al. |
| 5,470,337 | A |  | 11/1995 | Moss |
| 6,047,826 | A |  | 4/2000 | Kalinski et al. |

FOREIGN PATENT DOCUMENTS

| BR | 8202850 | 5/1982 |
| GB | 2198644 | 6/1988 |
| WO | 9212743 | 8/1992 |

* cited by examiner

*Primary Examiner*—Julian W. Woo

(57) ABSTRACT

A needle holder includes a base holder with a plurality of sockets therein for receiving and removably retaining the base of a needle in one of the sockets. A tip holder portion has a plurality of hollows therein in a common plane for receiving and removably retaining the tip of the needle. A stretcher member extends between the base holder and the tip holder and is preferably flexible to increase the variety of needle dimensions that can be accommodated in the holder. The needle holder is particularly suitable for the type of needle used in meniscal repair.

16 Claims, 4 Drawing Sheets

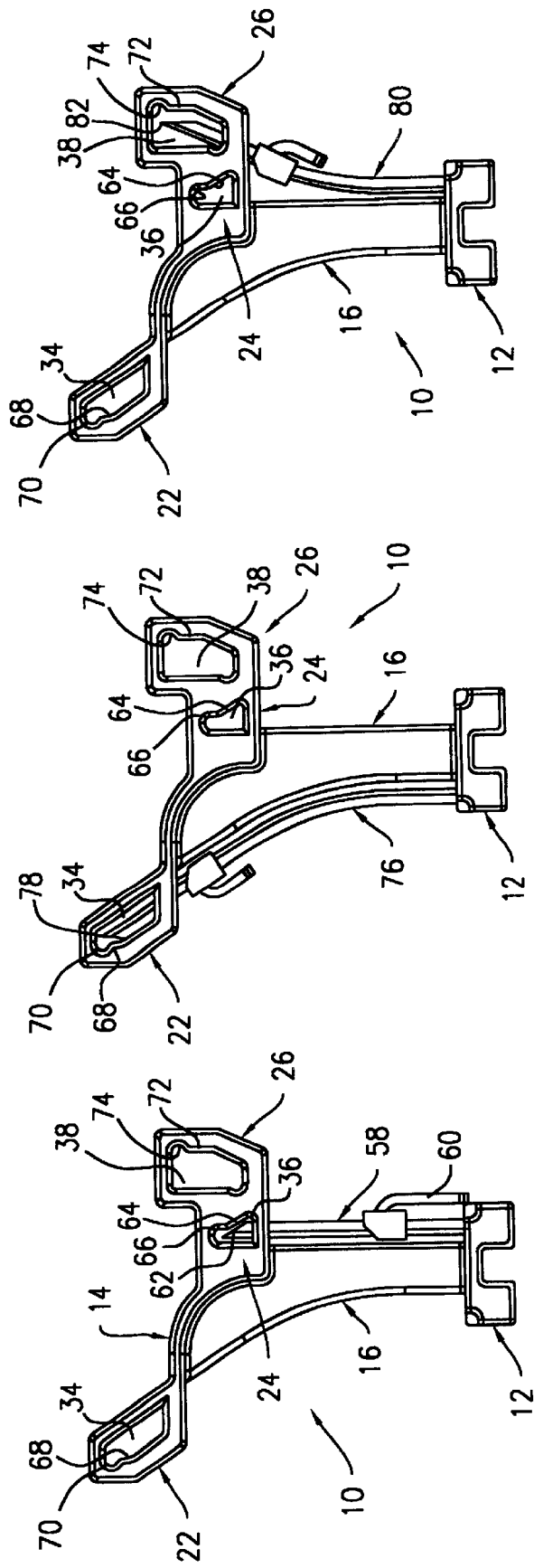

MULTI-POSITION MENISCAL NEEDLE HOLDER

FIELD OF THE INVENTION

The present invention relates to needle holders, and more particularly to holders suitable for holding needles used in meniscal and rotator cuff surgical repair.

BACKGROUND OF THE INVENTION

A specialized hollow needle is used in conjunction with a hand-held needle holder/ejector, hereinafter "ejector", to deliver H-shaped polymeric implant fasteners to the site of a torn meniscus for securing the edges of the tear or to repair the synovial/meniscal junction in accordance with known arthroscopic surgical techniques. A similar surgical method and instrument are utilized to repair torn rotator cuffs. Depending upon the surgical application, meniscal and rotator cuff needles differ in length and curvature. In order to perform the procedure, a disposable meniscal/rotator cuff needle having an associated H fastener is coupled to a mating ejector. After the procedure has been completed, the needle is decoupled for disposal and the ejector is kept for reuse. Meniscal needles are presently delivered from the manufacturer in plastic packages having friction-fit needle parks for retaining the needle in the package, e.g., as shown in U.S. Pat. No. 6,047,826.

Presently known needle holders most effectively hold needles of one specific shape and size. As a result, each needle type and size is preferably packaged in a unique mating package. The known prior art exhibits a need for provision of a needle package that may hold a selected one of a plurality of needle types in a substantially flat package, further allowing containment in a foil envelope having associated benefits of economy and effectiveness in maintaining sterility.

SUMMARY OF THE INVENTION

The problems and disadvantages associated with the conventional techniques and devices utilized to hold pointed objects are overcome by the present invention which includes a needle holder for holding needles having a pointed tip and a base for coupling to a hand-held needle holder/ejector device. The needle holder has a base holder portion with a socket therein for receiving and removably retaining the base of the needle. A tip holder portion with a hollow therein receives and removably retains the tip of the needle. A stretcher member extends between the base holder portion and the tip holder portion, the base holder portion being attached to the stretcher member at one end thereof and the tip holder portion being attached at the other end of the stretcher member.

BRIEF DESCRIPTION OF THE FIGURES

For a better understanding of the present invention, reference is made to the following detailed description of various exemplary embodiments thereof considered in conjunction with the accompanying drawings, in which:

FIGS. 2–4 are plan views of the needle holder of FIG. 1 with three different needles contained therein, respectively;

DETAILED DESCRIPTION OF THE FIGURES

Figure 1:
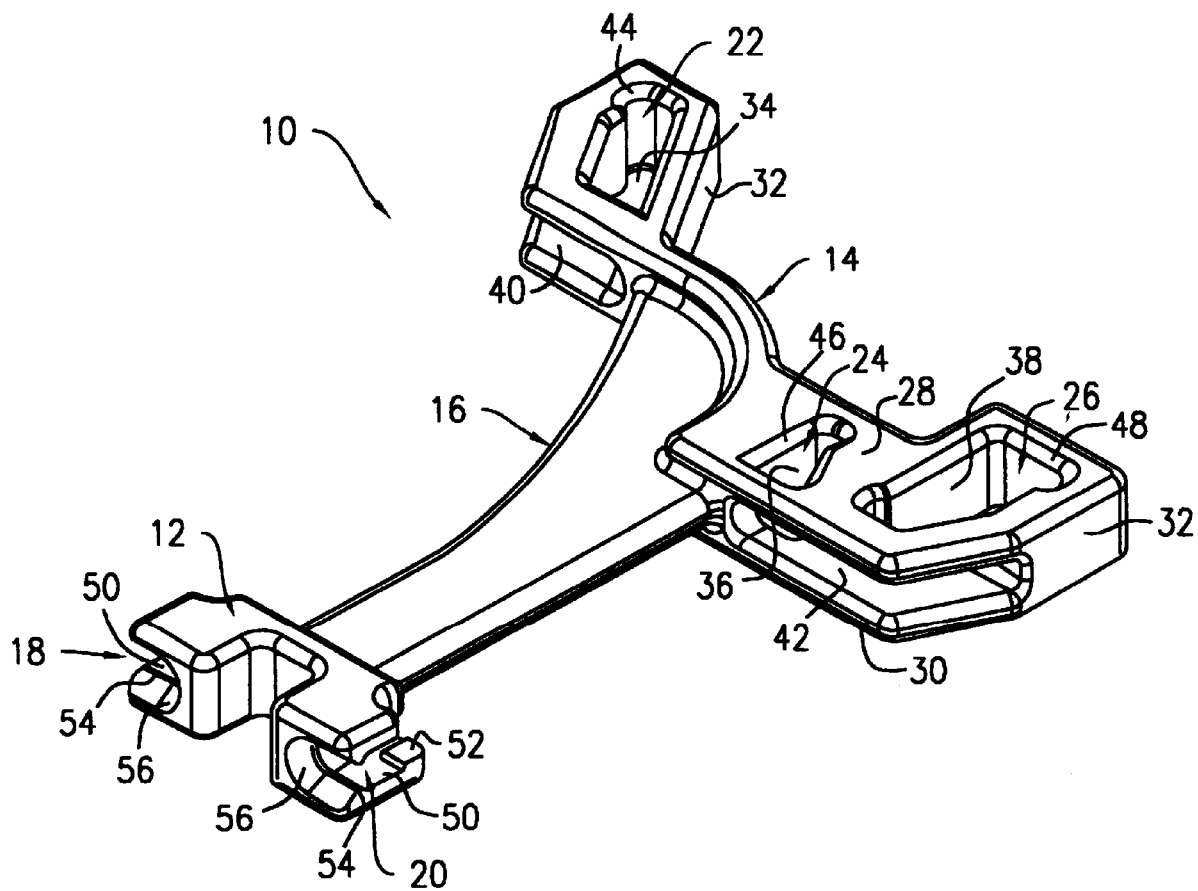
FIG. 1 is a perspective view of a needle holder in accordance with a first embodiment of the present invention.

FIGS. 1–4 show a needle holder 10 which is preferably monolithically injection molded or thermoformed from plastic such as polypropylene, polystyrene, polyethylene and equivalents thereof. The needle holder 10 has a base portion 12 for holding the base of a needle (e.g., 58 in FIG. 2). A needle tip holder 14 is positioned at a selected distance from the base 12 by stretcher 16. The base 12 has a pair of sockets 18, 20 for receiving and retaining an associated needle (e.g., 58, 76 as shown in FIGS. 2 and 3). The tip holder 14 has a plurality of needle tip cages 22, 24 and 26 for receiving and retaining an associated needle tip (e.g., 62 in FIG. 2). The tip holder 14 has a pair of opposed sidewalls 28, 30 and a peripheral outer wall 32 bridging therebetween and defining interior hollows 34, 36, 38. A lower slot 40 communicates with the hollow 34, while another lower slot 42 communicates with the hollows 36, 38, permitting, for example, the tip 62 of needle 58 to enter the hollow 36. The sidewalls 28, 30 may be provided with windows 44, 46, 48 proximate the cages 22, 24, 26 to save on material usage and to allow visualization of the needle tip (e.g., 62 as shown in FIG. 2). Alternatively, one or both of the sidewalls 28, 30 may be windowless.

The sockets 18, 20 of the base 12 each have a slot 50 formed between a raised block 52 and a raised lip 54 provided at the terminus of chamfer 56. The material from which the holder 10 is fabricated is preferably flexible and permits the sockets 18, 20 to be deformable under manual pressure. More particularly, the base of a needle to be held in the holder 10 can be inserted into the socket (e.g., 20) by deforming it slightly to permit it to slip past the raised block 52. Once inserted into the socket (e.g., 20), the needle is prevented from sliding out under its own weight by the raised block 52 and by the raised lip 54. The terminal chamfer 56 and raised lip 54 matingly interact with a conventional hand-held ejector (not shown) to facilitate positioning the ejector relative to the needle base for installing the needle onto the ejector. The open sockets 18, 20 permit a needle to be coupled to the ejector while the needle is still safely held within the holder 10 with the sharp point (e.g., 62) held in the tip holder 14. This prevents the pointed tip 62 from injuring the user of the device while it is being installed on the ejector.

FIG. 2 shows how a straight needle 58 (e.g. a needle used to repair a rotator cuff) is accommodated in the needle holder 10, namely, with the base of the needle 58 inserted into socket 20 (See FIG. 1) of base 12 and the beveled tip 62 extending into hollow 36 of cage 24. An abutment surface 64 is provided on the interior of the hollow 36 which is substantially parallel to the beveled tip 62, but does not extend as far as the tip 62, instead terminating upwardly in a point clearance area 66 that diverges away from the tip 62. In this manner, the needle is constrained in a longitudinal direction by the abutment surface 64 acting against the tip 62 and the lip 54 restraining the base of the needle 58. The point clearance area 66 shields the tip 62 of the needle from contacting the holder 10 and from being deformed in transit and prevents the needle from penetrating the holder 10.

FIG. 3 illustrates how another type of needle 76 (e.g. a curved needle used for meniscal repair and having a different shape and length than that of needle 58) may be accommodated in the needle holder 10. The tip 78 of needle 76 is constrained by abutment surface 68 which lies adjacent to point clearance area 70. Because the needle 76 is held within base slot 18 (See FIG. 1) it could be accommodated in the holder 10 simultaneously with needle 58 shown in FIG. 2. Although the intent of the present invention is to provide a holder that is suitable for use with a plurality of needles (i.e., used independently and stored singly in the holder 10), the capacity of the present invention to hold more than one needle can be utilized for procedures calling for a plurality of needles.

FIG. 4 shows yet another needle 80 stored in the holder 10. Needle 80 is curved like needle 76 of FIG. 3, but is of shorter length.

Figure 5:
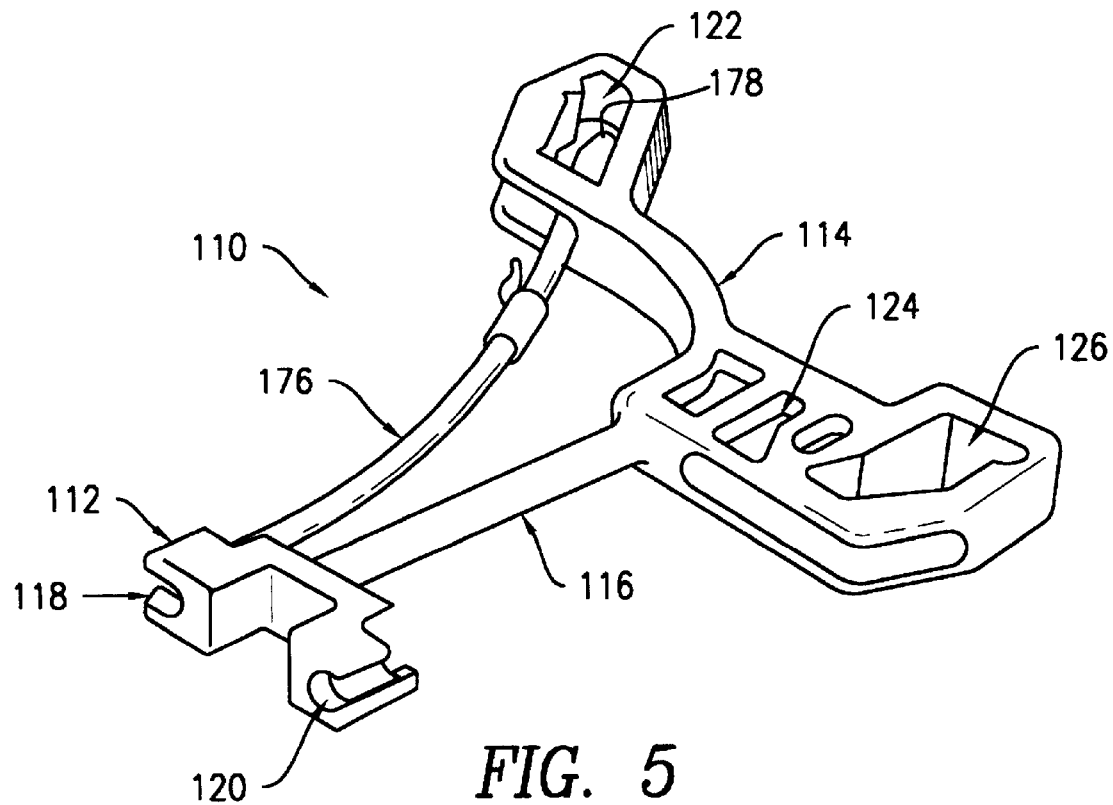
FIGS. 5 and 6 are perspective views of a needle holder in accordance with a second exemplary embodiment of the present invention.

FIG. 5 shows another form of needle holder 110 in accordance with the present invention and having substantially the same features as that of the embodiments described above in reference to FIGS. 1–4, viz., base 112 with sockets 118, 120 and tip holder 114 with tip cages 122, 124 and 126. The stretcher 116 is in the shape of an elongated column which may be formed monolithically with the remainder of the holder 100 from a plastic composition that is flexible, permitting the holder 110 to assume a plurality of positions. As shown in FIG. 5, the stretcher 116 is in a straight configuration resulting in the base 112 and the tip holder 114 having the same relative positions exhibited by the embodiment shown in FIGS. 1–4. A needle 176 having a similar curvature as the needle 76 shown in FIG. 3 is shown in position in the holder 110 with its base held in socket 118 and the tip 178 thereof held in tip cage 122.

Figure 6:
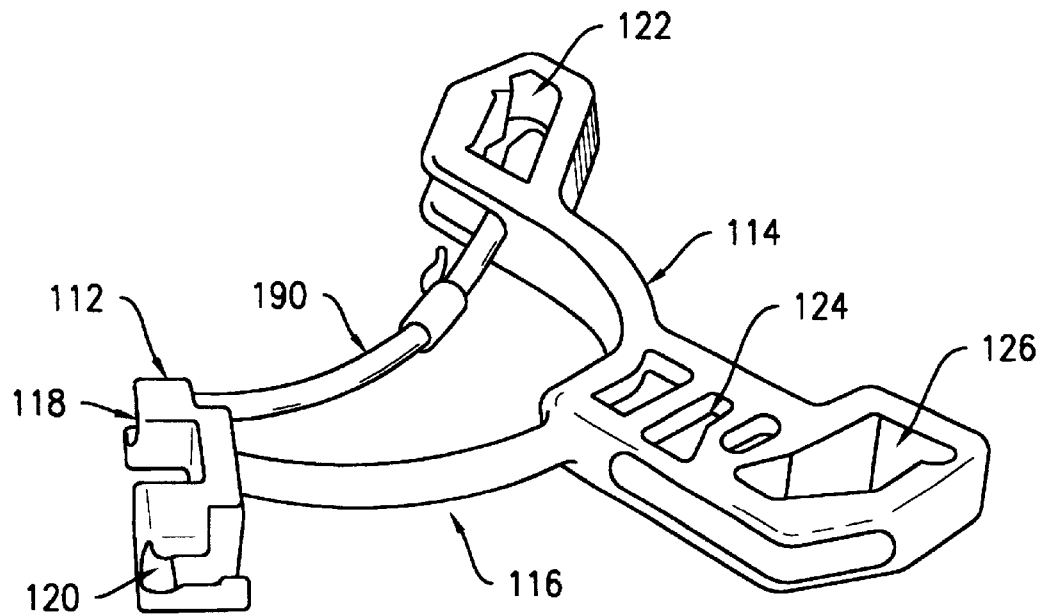

FIG. 6 illustrates that the stretcher 116 of the holder 110 can be bent to accommodate a different needle 190 with a different shape/size than needle 176, utilizing the same socket 118 and tip cage 122. The same adjustability is present with respect to socket 120 and tip cages 124 and 126. It should be appreciated from the foregoing that, while the present invention has been explained in reference to tip holders 14, 114 and base portions 12, 112 having multiple tip cages (e.g., 22, 24, 26) and multiple sockets (e.g., 18 20), respectively, the present invention can store a plurality of different size and shape needles by employing a flexible stretcher 116 such that multiple storage positions are not necessary to allow multi-purpose application.

Figure 7:
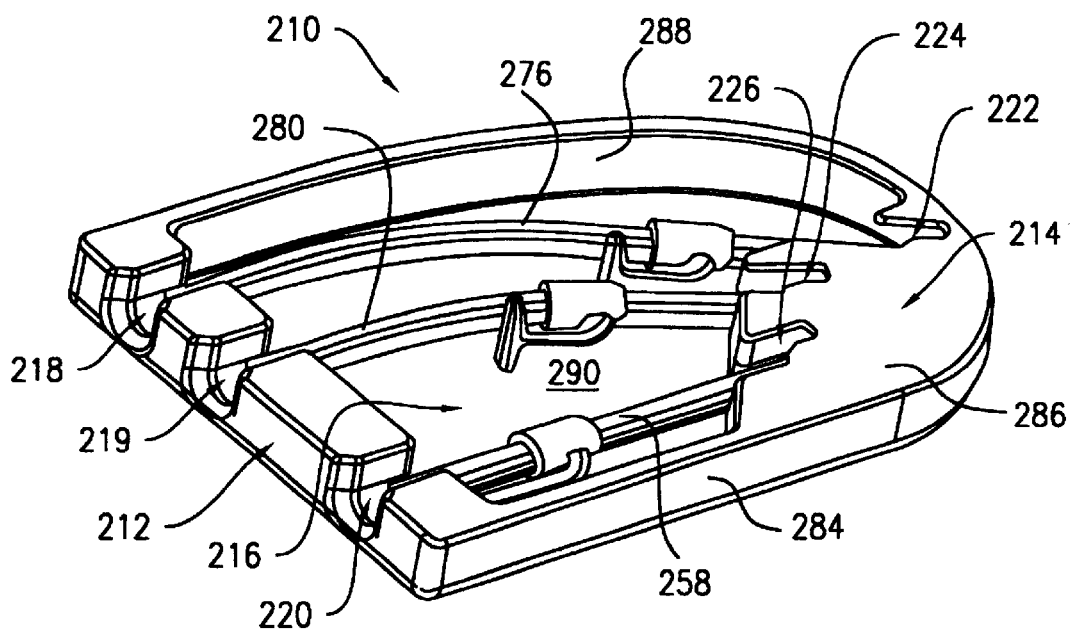
FIG. 7 is a perspective view of a needle holder in accordance with a third exemplary embodiment of the present invention.

FIG. 7 depicts a needle holder 210 in the form of a molded plastic tray having a base holder 212, a tip holder 214 and a stretcher structure 216 therebetween. The holder 210 has a peripheral sidewall 284 extending up to a top surface 286. A interior wall 288 descends from the top surface to a floor surface 290, with the convolutions of the interior wall 288 and its conjunction with the top surface 286 and floor surface 290 forming the tip holder 214. Sockets 218, 219 and 220 are provided in the base 212 and in conjunction with tip cages 222, 224 and 226, retain needles 258, 276 and 280 in the holder 210. As noted above, the holder 210 of the present invention may be utilized to hold one or a plurality of needles, as required by the surgical procedure for which it is used. After the needles to be held therein are deposited in the holder 210, the holder 210 is overlaid with an aluminum or Tyvek sheet which is adhered by adhesives or heat bonding to the top surface 286. The resultant enclosed package may then be placed within a further aluminum or Tyvek envelope for shipment. The needle holder 210, like the needle holders 10 and 110, can, along with all overwrapping, be sterilized using conventional methods, such as radiation, autoclaving, sterilizing gases and the like.

Figure 8:
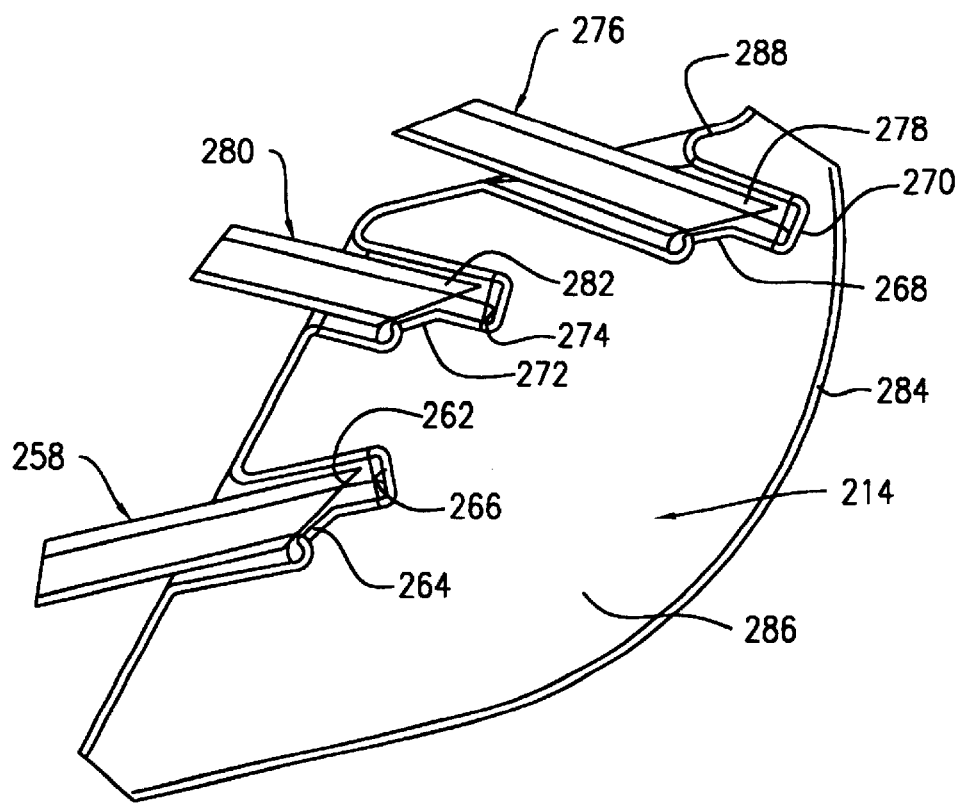
FIG. 8 is an enlarged view of a segment of the needle holder of FIG. 7.

FIG. 8 shows that the holder 210 utilizes point abutment surfaces 268, 264 and 274, as well as the point clearance areas 266, 270 and 274 in a similar manner and for the same purpose as described above in reference to FIGS. 1–4, these features being defined by sidewall 288.

It should be understood that the embodiments described herein are merely exemplary and that a person skilled in the art may make many variations and modifications without departing from the spirit and scope of the invention as defined in the appended claims. For example, while two base sockets 18, 20 and three tip cages 22, 24, 26 are depicted in FIG. 1, a greater or fewer number of either could be employed. Also, while a monolithically molded holder 10 is described above, a composite holder made from assembled parts (e.g., mating halves) could be utilized. All such variations and modifications are intended to be included within the scope of the invention as defined in the appended claims.

We claim:

1. A needle holder for holding a needle having a pointed tip and a base for coupling to a hand-held needle holder/ejector device, comprising:

a base holder portion with a socket therein for receiving and removably retaining the base of the needle;

a tip holder portion having a plurality of hollows therein to enable a plurality of differently dimensioned needles to be accommodated within said needle holder wherein each hollow is configured to receive and removably retain the tip of the needle; and a stretcher member extending between said base holder portion and said tip holder portion, said base holder portion being attached to said stretcher member at one end thereof and said tip holder portion being attached at the other end of said stretcher member.

2. The needle holder of claim 1, wherein said plurality of hollows are arranged in a common plane such that the thickness of the needle holder approximates the thickness attributable to a single hollow.

3. The needle holder of claim 2, wherein said socket can be used in conjunction with a first of said plurality of hollows for holding a first needle of a first configuration and said socket can be used in conjunction with a second of said plurality of hollows for holding a second needle of a second configuration.

4. The needle holder of claim 3, wherein the first needle has a different shape than the second needle.

5. The needle holder of claim 4, wherein said first hollow is defined by a front wall, a substantially parallel back wall spaced from said front wall and a peripheral wall bridging between said front wall and said back wall, said peripheral wall having a slot therein communicating with said hollow and directed generally in the direction of said base holder portion, said slot receiving the needle therethrough such that the tip of the needle can be contained in said first hollow when held in said needle holder.

6. The needle holder of claim 5, wherein said front wall has an opening therein for viewing the tip of the needle when the needle is in place within said hollow.

7. The needle holder of claim 5, wherein the spacing between said front wall and said back wall approximates the thickness of a needle held in said needle holder, whereby said needle holder prevents curved needles from twisting out of parallel to said plane.

8. The needle holder of claim 2, wherein said base holder portion has a plurality of sockets.

9. The needle holder of claim 8, wherein said sockets are distributed on either side of said stretcher member, said needle holder being generally I-shaped with said base holder portion corresponding to the lower horizontal line of the I, said stretcher member corresponding to the vertical line of the I and said tip holder portion corresponding to the upper horizontal line of the I.

10. The needle holder of claim 9 wherein said stretcher member is an elongated flattened beam.

11. The needle holder of claim 9, wherein said stretcher member has an elongated substantially tubular shape which is bendable under finger pressure.

12. The needle holder of claim 9, wherein said needle holder is a thermoformed tray with said base holder portion and said tip holder portion being formed integrally with said tray and projected up from a floor of said tray.

13. The needle holder of claim 12, wherein said tray and a needle contained therein are covered by a cover sheet.

14. The needle holder of claim 2, wherein each of said plurality of hollows has a point relief area and a tip abutment area, said tip abutment area abutting against a bevel at the tip of the needle when the needle is held in said needle holder, said bevel converging distally to a sharp point, said point relief area disposed proximate to said abutment area and including an extension of said hollow to accommodate the point of the needle such that the point does not contact said needle holder.

15. The needle holder of claim 1, wherein said stretcher member is manually bendable to permit the adjustment of the alignment of said hollow relative to said socket, whereby needles having different configurations can be contained in said needle holder.

16. A needle holder for holding a needle having a pointed tip and a base for coupling to a hand-held needle holder/ejector device, comprising:

a base holder portion with a socket therein for receiving and removably retaining the base of the needle;

a tip holder portion with a hollow therein for receiving and removably retaining the tip of the needle;

a stretcher member with an elongated substantially cylindrical shape and a longitudinal axis, which is bendable under finger pressure, extending between said base holder portion and said tip holder portion, said base holder portion being attached to said stretcher member at one end thereof and said tip holder portion being attached at the other end of said stretcher member, wherein the longitudinal axis of said stretcher member is configured to be disposed to a side of the needle retained by said socket and said hollow.

* * * * *